(12) United States Patent
Krokhin et al.

(10) Patent No.: US 8,501,487 B2
(45) Date of Patent: Aug. 6, 2013

(54) COMPOSITION FOR USE AS A PEPTIDE RETENTION STANDARD AND A METHOD OF PREDICTING PEPTIDE HYDROPHOBICITY IN LIQUID CHROMATOGRAPHY

(75) Inventors: Oleg V. Krokhin, Winnipeg (CA); Vic Spicer, Winnipeg (CA)

(73) Assignee: University of Manitoba, Winnipeg (CA)

( * ) Notice: Subject to any disclaimer, the term of this patent is extended or adjusted under 35 U.S.C. 154(b) by 65 days.

(21) Appl. No.: 13/130,090

(22) PCT Filed: Nov. 30, 2009

(86) PCT No.: PCT/CA2009/001730
§ 371 (c)(1),
(2), (4) Date: May 19, 2011

(87) PCT Pub. No.: WO2010/060218
PCT Pub. Date: Jun. 3, 2010

(65) Prior Publication Data
US 2011/0219858 A1 Sep. 15, 2011

Related U.S. Application Data

(60) Provisional application No. 61/118,546, filed on Nov. 28, 2008.

(51) Int. Cl.
*G01N 31/00* (2006.01)
(52) U.S. Cl.
USPC .......................................................... 436/86
(58) Field of Classification Search
USPC .......................................................... 436/86
See application file for complete search history.

(56) References Cited

PUBLICATIONS

Oleg B. Krokhin, Vic Spicer, "Peptide Retention Standards and Hydrophobicity Indexes in Reversed-Phase High-Performance Liquid Chromatography of Peptides", Analytical Chemistry, Vo. 81, No. 22, Nov. 15, 2009, 9522-9530.
Valko and Slegel, "New chromatographic hydrophobicity index based on the slope and the Intercept of the log k' versus organic phase concentration plot", Journal of Chromatography. 1993, vol. 631, 49-61.
Eyers et al., "Qcal—A Novel Standard for Assessing Instrument Conditions for Proteome Analysis", American Society for Mass Spectrometry, vol. 19 (9), Sep. 2008, 1275-1280.
Guo, Dacheng, Mant, Colin T., Ashok, K. Taneja, Hodges, Robert S. , "Prediction of Peptide Retention Times In Reversed-Phase High-Performance Liquid Chromatography II. Correlation of Observed and Predicted Peptide Retention Times and Factors Influencing the Retention Times of Peptides", Journal of Chromatography, 359 (1986), 519-532.
Guo, Dacheng, Mant, Colin T., Taneja, Ashok K., Parker J.M. Robert, Hodges, S. Hodges, "Prediction of Peptide Retention Times in Reversed-Phase High-Performance Liquid Chromatography I. Determination of Retention Coefficients of Amino Acid Residues of Model Synthetic Peptides", Journal of Chromatography, 359, (1986), 499-518.

*Primary Examiner* — Monique Cole
(74) *Attorney, Agent, or Firm* — Bereskin & Parr LLP/S.E.N.C.R.L., s.r.l.; Patricia Folkins

(57) ABSTRACT

A composition comprising synthetic peptides for use as a peptide retention standard in liquid chromatography applications is disclosed Said synthetic peptides have a broad range of hydrophobicity while maintaining low variation in their molecular weights The synthetic peptides disclosed consist of the ammo acid sequences LGGGGGGDGSR, LGGGGGDFR, LLGGGGDFG, LLLGGDFR, LLLL-DFR, LLLLLDFR A method of predicting the hydrophobicity of an unknown peptide in liquid chromatography using a composition of peptide retention standards and a method of developing a Universal Hydrophobicity Index (UHI) for the measurement of peptide hydrophobicity in liquid chromatography are also described.

7 Claims, 4 Drawing Sheets

COMPOSITION FOR USE AS A PEPTIDE RETENTION STANDARD AND A METHOD OF PREDICTING PEPTIDE HYDROPHOBICITY IN LIQUID CHROMATOGRAPHY

CROSS-REFERENCE TO RELATED APPLICATIONS

This application is a National Stage of International Application No. PCT/CA2009/001730, filed on Nov. 30, 2009, which claims the benefit of priority from U.S. Provisional Application No. 61/118,546, filed on Nov. 28, 2008, the contents of which are incorporated herein by reference in their entirety.

INCORPORATION OF SEQUENCE LISTING

A computer readable form of the Sequence Listing "9157-P33171US01_SequenceListing.txt" (8,192 bytes), submitted via EFS-WEB and created on Feb. 12, 2013, is herein incorporated by reference.

FIELD OF THE INVENTION

The present disclosure relates to a composition for use as a peptide retention standard. The disclosure also relates to a method of predicting peptide hydrophobicity in liquid chromatography (LC). The disclosure further relates to a method of determining a Universal Hydrophobcity Index (UHI).

BACKGROUND OF THE INVENTION

High-Performance Liquid Chromatography (HPLC) of biological macromolecules has been a field of intensive research and the inspiration for several generations of separation scientists. Peptide LC separation science matured both theoretically and practically during the 1980's-1990's.[1-3] When recent advances in mass spectrometry led to significant breakthroughs in protein/peptide analysis (often regarded as "omics" era), the chromatographic counterpart was ready to accommodate these new challenges. Indeed, the optimal separation conditions for peptide mixtures are "common knowledge" and used with only slight variations in many proteomics laboratories: a 0-60% acetonitrile gradient with trifluoroacetic acid (TFA) as ion-pairing modifier is recommended for the separation of peptide mixtures.[4]

Simultaneously, the basic questions of LC separation techniques are approached very differently by "classic" HPLC studies and "modern" proteomics/peptidomics applications. For LC specialists, peptide separation selectivity is a primary criteria, since detection options traditionally were limited to mostly spectrophotometric detection. Separation conditions were varied to try to optimize complete peak resolution. Conversely, the use of powerful mass-spectrometry detection in proteomics allows the simultaneous identification of co-eluting species, shifting the emphasis to providing better separation efficiency and optimal sampling rate (peak capacity) for mass detectors.

Despite a basic (or certain) negligence towards resolving the fundamental questions of selectivity optimization, selectivity prediction will become an important part of proteomics protocols in the future. Peptide retention (i.e. selectivity) prediction can be used as an additional filter to harden protein/peptide identification in bottom-up proteomics studies,[5-7] to decrease the time required for analysis,[8] and to even direct the choice of optimal separation systems for a particular sample.[9]

Recent developments in the field were fuelled by the abundant availability of peptide sequence-retention data sets. A number of peptide retention prediction models have been reported in past few years,[10-18] building on earlier work from the 1980's-1990's.[16-19] These recent attempts served to add knowledge of peptide separation to classical HPLC. Specifically there were definite improvements in understanding the ion-pairing separation mechanism,[10] it's influence on apparent hydrophobicity of amino acid side chains (especially at N- and C-termini),[20] the affect of the residue position within peptide chain,[13] and the propensity to form helical structures.[11] This information resulted in significant improvements of peptide retention prediction accuracy: correlations of $R^2$-value ~0.98 have been demonstrated,[11,13] while the "classical" additive approach cannot exceed $R^2$~0.93 in real proteomics samples.

One might speculate that the virtually unlimited datasets being filled by mass-spectrometry MS/MS peptide identification would ultimately render predictive models unnecessary, as all retention characteristics for all possible peptides would eventually be experimentally determined. But there are significant barriers preventing this from happening soon. First, while majority of proteomics researchers deal with the separation of tryptic peptides, there is a large number of non-tryptic species formed in-vivo and even during the trypsin digestion. Adding chemical and post-translation protein/peptide modifications makes it difficult to estimate the number of species one might deal with during proteomics experiments, let alone evaluating the probability of detecting all of them. Second, there are a large number of variations in mobile/stationary phases used in proteomics LC. There are many commercial suppliers of RP-separation media, and these products are the subject of ongoing improvements and modifications. There are several variations of mobile phase composition: for example, ESI-, MALDI-compatible and high pH RP for 2-dimensional schemes. Different separation systems will require collection of separate data sets. Third, it is unlikely that such vast amount of information can be collected in one laboratory or even using one LC experimental platform. It will require collective efforts from the proteomics community, making the issue of a "standardized" alignment of LC-MS data critical. Finally, peptides represent the group of "irregular" solutes from the linear-solvent-strength (LSS) point of view.[4] In other words, the slopes (S) in the fundamental LSS equation are different for different peptides:

$$\log k = \log k_w - S^* \phi \qquad (1)$$

where k is capacity factor at organic solvent volume fraction $\phi$ and $k_w$ is the capacity factor at $\phi=0$. It was shown that this could result in selectivity variation and even reverse the elution order based on different column sizes, gradient steepness values and flow rates.[21] This will create discrepancies during the transfer of retention information, even between systems with identical stationary/mobile phase combinations.

All these issues need to be considered in this new "proteomics/peptidomics" stage of peptide HPLC research. Recently, peptide separation selectivity of 300 Å and 100 Å sorbents, and of C18 phases and C18 materials with embedded polar groups was compared. This study included screening of a number of commercial C18 phases and switching the ion-pairing modifiers to monitor changes in selectivity.[22] Studies like this help at least determine a few groups of phases/conditions where predictive models and data sets can be considered transferable.

Another important problem is the accurate alignment of LC-MS data. Spiking the samples with a mixture of known peptides, or monitoring retention times (RT) of the redundant species present in different LC-MS runs is a common practice. Petritis et al. followed the retention of six peptides frequently observed in *D. radiodurans* and *S. oneidensis* to align 687 different LC-MS/MS runs.[23] When dealing with the samples from non-related organisms, spiking the analyzed mixture with known peptides is required. In other work human transferrin was added to all of the protein mixtures used to collect peptide retention data sets for the model optimization. Following tryptic digestion it produced ~35 easily detectable peptides; which were used to draw RT vs. calculated hydrophobicity (H) linear plots and to align the data to adjust for small changes in slopes and intercepts. Later, a simpler digest of horse heart myoglobin was used for the same purpose.[11] It was also proposed to use the extrapolated (on combined RT vs. H plots for the optimization data set) "ideal hydrophobicity" values of these standard peptides. Finding retention times of target peptides in each LC run allows a very robust chromatographic calibration and data alignment. An alternative approach is to use a number of confidently MS/MS identified peptides to plot RT vs. H as a calibration.[15, 24] However, the accuracy of this procedure is dependent on the elimination of false-positive identifications and retention prediction accuracy for particular set of peptides.

A peptide retention standard for RP HPLC of peptides was developed for commercial use, and contains a mixture of five synthetic C-terminal amide decapeptides of the generic formula: [Ac-Arg-Gly-X-X-Gly-Leu-Gly-Leu-Gly-Lys-Amide] [SEQ ID NO:1].[25] Sequence variations of [X-X] are [Gly-Gly], [Ala-Gly], [Val-Gly] and [Val-Val]. The fifth peptide contains the [Ala-Gly] sequence plus a free N-terminal amino group. Molecular weights of these species ranged between 883-995 Da, making them easily detectable by both ESI and MALDI MS techniques. The disadvantage of this mixture is a narrow range of hydrohobicities—~6% on acetonitrile percentage scale, whereas typically tryptic peptides elute within a ~40% window. Recently Eyers et al.[26] developed a peptide standard to address the performance of LC-MS systems as a whole including separation and detection parts. They generated artificial protein QCAL, which provides a set of 22 peptides of various sizes and hydrophobicities upon tryptic digestion.

Another issue closely related to retention standard development is how the value of peptide hydrophobicity is expressed and used in chromatographic experiments. Thus, the Sequence Specific Retention Calculator (SSRCalc) model plots dependencies of RT vs. calculated hydrophobicity, with the latter being a product of multiple factors reflecting the influence of amino acid sequence, pI and propensity to form helical structures.[11] This value has no connection to any physical property of separated species unless it's related to the hydrophobicity of standard peptide(s). An alternative way to represent retention prediction data is the use of normalized retention/elution time (NRT/NET) values.[12,23] While this approach normalizes retentions to a set of known peptides, these values don't express real chromatographic properties of the species either, unless the standard peptides are well characterized.

While the general concept of hydrophobicity of peptides and proteins is well understood, this field is known for the large number of hydrophobicity scales.[27-29]

SUMMARY OF THE INVENTION

A new standard peptide composition has been developed and used to calibrate HPLC experiments. Furthermore it has been determined that hydrophobicity of a peptide can be defined in Universal Hydophobicity Units (UHI) wherein the UHI describes the concentration of organic solvent for any peptide that yields a set capacity factor, for example 10, under isocratic elution conditions.

According to an aspect of the present disclosure there is included a composition comprising the following peptides:

| | |
|---|---|
| LGGGGGGDGSR; | [SEQ ID NO: 2] |
| LGGGGGGDFR; | [SEQ ID NO: 3] |
| LLGGGGDFR; | [SEQ ID NO: 4] |
| LLLGGDFR; | [SEQ ID NO: 5] |
| LLLLDFR; and | [SEQ ID NO: 6] |
| LLLLLDFR. | [SEQ ID NO: 7] |

According to another aspect of the disclosure there is provided a kit for use as a standard for peptide chromatography comprising a composition described above and instructions for use.

According to a further aspect of the disclosure there is provided a method of predicting hydrophobicity of a peptide under selected liquid chromatographic conditions comprising:

(a) measuring retention time for each peptide of a standard peptide mixture at three or more different concentrations of acetonitrile under isocratic conditions;

(b) calculating a retention coefficient k for each peptide in the mixture and at each concentration of acetonitrile using equation (2)

$$k=(t_R-t_O)/T_{Oc} \qquad (2)$$

wherein
$t_R$ is the retention time,
$t_O$ is system dead time, and
$T_c$ is column dead time;

(c) for each peptide in the mixture, plotting log k vs $\phi$, wherein $\phi$ is the acetonitrile volume fraction;

(d) for each peptide in the mixture, determining the value of $\phi$ when log k=1 and converting this to acetonitrile concentration to provide a universal hydrophobicity index (UHI);

(e) plotting retention times of each peptide vs its UHI;

(f) determining the retention time of an unknown peptide under the isocratic liquid chromatographic conditions; and (g) determining from the plot in (e) the value of UHI that corresponds to the retention time of the unknown peptide, wherein the UHI correlates to the hydrophobicity of the unknown peptide.

It is an embodiment of the disclosure that the standard peptide mixture is a composition comprising one or more of the following peptides:

| | |
|---|---|
| LGGGGGGDGSR; | [SEQ ID NO: 2] |
| LGGGGGGDFR; | [SEQ ID NO: 3] |
| LLGGGGDFR; | [SEQ ID NO: 4] |
| LLLGGDFR; | [SEQ ID NO: 5] |

| | | |
|---|---|---|
| LLLLDFR; and | [SEQ ID NO: 6] | |
| LLLLLDFR. | [SEQ ID NO: 7] | |

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The disclosure will now be described in greater detail with reference to the drawings in which.

DETAILED DESCRIPTION OF THE INVENTION

Definitions

Figure 1:
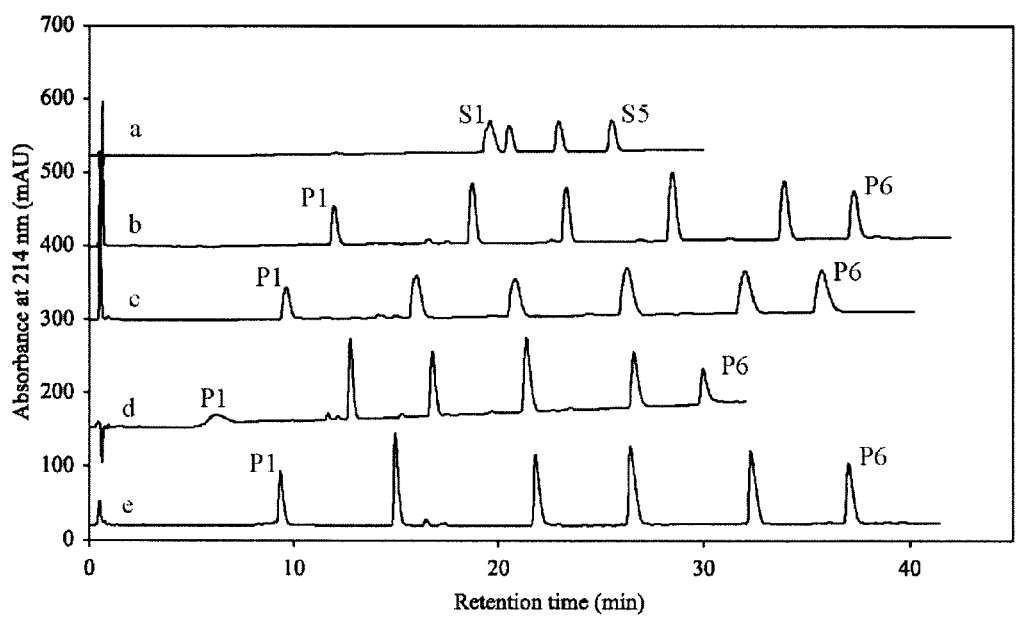
FIG. 1 is a graph showing chromatographic separations of a prior art standard peptide mixture S1-S5 (a) and a 6-peptide mixture according to one embodiment of the present disclosure (b-e) using 150 µl/min flow-rate, 1 mm×100 mm columns size and 1% acetonitrile per minute gradient. a, b) 100 Å (Luna C18(2)) 0.1% TFA, c) 300 Å (Vydac TP218) 0.1% TFA, d) 100 Å (Luna C18(2)) FA, e) 100 Å (XTerra) pH 10.

The following abbreviations are used throughout the disclosure and have their standard meanings known in the art:
Natural Amino Acids:

| | | |
|---|---|---|
| Alanine | ALA | A |
| Cysteine | CYS | C |
| Aspartic Acid | ASP | D |
| Glutamic Acid | GLU | E |
| Phynylalanine | PHE | F |
| Glycine | GLY | G |
| Histidine | HIS | H |
| Isoleucine | ILE | I |
| Lysine | LYS | K |
| Leucine | LEU | L |
| Methionine | MET | M |
| Asparagine | ASN | N |
| Proline | PRO | P |
| Glutamine | GLN | Q |
| Arginine | ARG | R |
| Serine | SER | S |
| Threonine | THR | T |
| Valine | VAL | V |
| Tryptophan | TRP | W |
| Tyrosine | TYR | Y |

RT means retention time and means the elapsed time between the time of injection of a substance and the time of elution of the corresponding peak in chromatography.

RP means reversed phase.

LC means liquid chromatography.

HPLC means high performance liquid chromatography.

ACN % means percent acetonitrile and refers to the amount in percent by volume of acetonitrile in the eluent.

TFA means trifluoroacetic acid.

FA means formic acid.

MALDI means matrix assisted laser desorption ionization.

ESI means electrospray ionization.

MS means mass spectrometry.

The term "isocratic conditions" as used herein means that the composition of the eluent remains constant throughout the chromatographic run.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Compositions of the Disclosure

Design of a Standard Peptide Mixture

The use of purified synthetic peptides is preferred for LC-MS alignment. Real tryptic digests often contain products of non-specific cleavage and extraneous impurities. Developing a unified standard will significantly simplify the data transfer and comparison between different laboratories and LC systems. An optimal peptide retention standard (peptide mixture) should, for example: i) uniformly cover a wide range of peptide hydrophobicities similar to real proteomics samples; ii) be easily detectable by conventional MS equipment (e.g. have suitable molecular weights and ionization properties); iii) not interfere with the MS/MS identification of the analyzed sample or create false-positive identifications; and iv) not contain peptides prone to chemical modifications (e.g oxidation, deamidation, N-terminal cyclization, etc.).

The HLPC-MALDI MS technique is a primary tool used for the detailed analysis of protein samples. Therefore the development of peptide retention standard in the present disclosure was directed towards TFA-based eluent systems. The SSRCalc model correlates observed retention time of peptides with calculated hydrophobicity. These calculated hydrophobicity values span ~-7-56 for 100 Å TFA, and 0-65 for 300 Å TFA versions of the algorithm. Both optimization datasets contain ~5000 peptides and represent a typical set of tryptic peptides, which researchers would see during a bottom-up proteomics analysis. Therefore the optimal standard mixture should uniformly cover most of the hydrophobicity scale of ~65 SSRCalc units. Table 1 shows the peptide sequences that were selected for the present disclosure. In choosing these sequences some additional criteria was applied beyond those discussed in the above:

1) The molecular weight of model peptides was kept below 900 Da. The GPM (X!Tandem™) search engine is normally used for protein identification by MS/MS. It rarely assigns high confidence scores for species with low molecular weight. This gives additional insurance that calibrating peptides will not produce false positive identifications.

2) Aim to keep the same (or close) molecular weight for all the peptides. This simplified assigning this species on complex TIC chromatograms. The substitution of -Gly-Gly- for -Leu- was one possibility: it causes a 0.959 Da decrease in mass but substantial increase in hydrophobicity; this alters the retention of the peptide while keeping the mass nearly constant. Substitution -Gly-Ser- for -Phe- (between peptides 1 and 2) gave a similar result with +3.015 Da mass shift.

3) Attempted to encode a common sequence motif, which provided the same fragment ion upon MS/MS fragmentation. This made it easier to assign the peaks in precursor ion scan mode or MRM transition analysis. It is known that the C-terminal peptide bond adjacent to Asp typically produces intense y fragments. Therefore, most of the peptides herein have a -DFR N-terminal sequence and consequently a prominent y2 (322.188 Da) fragment. The only exception is peptide #1 with -DGSR sequence and 319.173 Da y3 daughter ion.

The selected peptide sequences, their observed m/z values for typical MALDI/ESI conditions and calculated hydrophobicities are shown in Table 1. Most of the above-listed ideal conditions were met, with ~40 SSRCalc hydrophobicity units covered by these peptides. While it is possible to add more species with lower and higher retention values, the former ones will tend to elute under isocratic conditions at the beginning of chromatogram and the latter will have problems with solubility and recovery from the C18 separation media.

FIG. 1 shows a UV chromatogram of S1-S5 standards from Pierce (100 Å, TFA conditions) and the peptide standard mixture of the present disclosure (P1-P6) using four common RP LC combinations: 100 Å-TFA; 300 Å-TFA; 100 Å-FA and 100 Å-pH 10. A one percent per minute acetonitrile gradient starting from 0% was used for all separations. The retention time difference between first and last peaks on chromatograms gives direct indication of ACN % scale covered. FIG. 1a,b shows that the S1-S5 mixture elutes over ~6% acetonitrile concentration range from the Luna C18(2) column, and the 6-peptide standard elutes over ~26%. Such wide coverage is very important, especially for nano- and microflow proteomics LC applications. While normal-flow gradient system technology is well established, in nano scale LC gradient reproducibility is harder to achieve. The correct retention time distribution of the standard peptides of the present disclosure confirms the proper development of the gradient, especially at the beginning of the chromatogram. Also note the uniform distribution of the six peaks of the peptide composition of the present disclosure throughout the chromatogram; such uniformity is rarely observed in standard peptide mixtures derived from protein digests.

The column size, flow rate and gradient steepness were the same for all of the chromatograms in FIG. 1 and therefore this represents a very good illustration of the differences in peptide hydrophobicity provided by switching ion-pairing modifiers and pore sizes. For example, changing from 100 Å to 300 Å (b and c) slightly decreased the retention times with no apparent change in selectivity. Conversely, the application of FA instead of TFA decreased the retention significantly (b and d) to the point where peptide #1 elutes under isocratic conditions of 0% acetonitrile, an example of peak shape distortion discussed previously. At pH 10 conditions, with ammonium formate as eluent additive, the ammonium cations served as counterparts in ion-pairing interactions with the negatively charged side chains of -Asp- and C-termini. Due to hydrophilic nature of $NH_4^+$, one might expect that hydrophilic P1 and perhaps P2 will not be retained at 0% acetonitrile. In-fact, they both elute under gradient conditions (FIG. 1c) with good peak shape. While not wishing to be limited by theory, this is the consequence of having neutral N-termini at pH 10, thus removing the "ion-pairing screen" from the hydrophobic -Leu- residues and increasing their apparent hydrophobicity and the overall retention of the peptides.

FIG. 1 clearly indicates that all six analytes in the designed standard mixture of the present disclosure elute from RP columns under gradient conditions in all four mobile/stationary phase combinations and cover wide ACN % scale. The only exception is peptide P1 with formic acid as ion-pairing modifier.

Accordingly, the present disclosure includes a composition comprising one or more of the following peptides:

```
LGGGGGGDGSR;      [SEQ ID NO: 2]

LGGGGGGDFR;       [SEQ ID NO: 3]

LLGGGGDFR;        [SEQ ID NO: 4]

LLLGGDFR;         [SEQ ID NO: 5]

LLLLDFR;          [SEQ ID NO: 6]
and

LLLLLDFR.         [SEQ ID NO: 7]
```

In an embodiment of the disclosure, the composition comprises two, three, four, five or six of the above-listed peptides. In a further embodiment the composition comprises all six of the above-listed peptides.

In an embodiment of the disclosure, the composition consists of the following peptides:

```
LGGGGGGDGSR;      [SEQ ID NO: 2]

LGGGGGGDFR;       [SEQ ID NO: 3]

LLGGGGDFR;        [SEQ ID NO: 4]

LLLGGDFR;         [SEQ ID NO: 5]

LLLLDFR;          [SEQ ID NO: 6]
and

LLLLLDFR.         [SEQ ID NO: 7]
```

The peptides of the disclosure are prepared, for example, by chemical synthesis using techniques known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

According to an embodiment of the present disclosure, the peptides are synthesized by step-by-step building of the peptide chain beginning with the C-terminal amino acid. The process involves maximum blocking of functional groups, starting from an amino acid alkyl ester, using the method of active esters.

In a suitable embodiment, the method involves the blocking of the amino, carboxyl and other reactive side groups of the amino acid(s) which are known to react during the synthesis. Suitable blocking agents are known to a person skilled in the art. For example, a suitable carboxy blocking agent include, without limitation, ethyl, nitrobenzyl, and t-butyl. A suitable amino blocking agent include, without limitation, fluorenylmethoxycarbonyl (Fmoc), carbobenzoxy, tosyl, trifluoracetyl and, suitably, t-butyloxycarbonyl (Boc). The amino acids are then coupled and the blocking agents subsequently removed. The peptide is optionally further purified using reverse phase chromatography.

The peptides of the disclosure are also prepared, for example, using standard recombinant DNA technology by transforming a suitable cell with a DNA molecule encoding the peptide and expressing the peptide in the cell and isolating the peptide. Such techniques are well known in the art (see for example, Maniatis, T., Fritsch, E. F., and Sambrook, J. (1982) Molecular Cloning: A Laboratory Manual, Cold Spring Harbor Laboratory, Cold Spring Harbor, N.Y.).

The composition of the present disclosure may also be incorporated in to a kit. In an embodiment the kits comprises one, two, three, four, five or six, suitably six, of the following peptides:

| | |
|---|---|
| LGGGGGGDGSR; | [SEQ ID NO: 2] |
| LGGGGGGDFR; | [SEQ ID NO: 3] |
| LLGGGGDFR; | [SEQ ID NO: 4] |
| LLLGGDFR; | [SEQ ID NO: 5] |
| LLLLDFR; and | [SEQ ID NO: 6] |
| LLLLLDFR. | [SEQ ID NO: 7] | and instructions for use.

In an embodiment the instructions describe the use of the peptides as a standard for liquid chromatography, suitably RP liquid chromatography, more suitably RP HPLC. In a further embodiment, the kit comprises reagents and materials for use in liquid chromatography, suitably RP liquid chromatography, more suitably RP HPLC.

Universal Hydrophobicity Index

Operationally the role which surrounding environment (i.e. pH, ionic strength, interacting partners, etc.) plays upon protein interactions adds more difficulty in quantifying hydrophobicity. Peptide RP HPLC has a chance to avoid this fate: interaction occurs on artificially and reproducibly manufactured hydrophobic surfaces under strictly controlled conditions of various ion-pairing environments. Therefore educated selection of compatible RP HPLC provides conditions for better standardization and developing universal hydrophobicity scales (at least on a peptide level). There is only one common variable in all these systems—continually changing concentration of organic solvent. This parameter is the most attractive and natural to express peptide hydrophobicity in RP HPLC.

Hydrophobicity in acetonitrile concentration (ACN %) units can be measured under both gradient and isocratic conditions. Thus, knowing retention time, gradient delay time and slope of the gradient allows one to determine the ACN % at which a particular component elutes from the column. For the gradient of 1% acetonitrile per minute, hydrophobicity can be expressed in time units. For the additive retention prediction models, the intrinsic hydrophobicities (retention coefficients) of individual residues can be expressed in time units as well. More importantly, the ACN % scale allows the simple transfer of the methods between gradient and isocratic modes. Once the acetonitrile concentration at which a component of interest leaves the column is determined, it can be used to design preparative method, which employs a very shallow gradient or an isocratic separation. This conversion, however, may result in significant errors due to specific character of gradient elution as recently highlighted by Snyder & Dolan.[4] During RP HPLC gradient elution peptides start to move through the column with increasing speed. This acceleration is different for different peptides due to variation of S values in LSS eqn. 1. In fact gradient slope, flow rate and size of the column will affect assignment of ACN % peptide hydrophobicity under gradient conditions.

The use of isocratic elution is therefore preferable for this purpose, as peptide retention will depend only on the type of sorbent, the nature and concentration of ion-pairing modifier and the temperature.

Accordingly, in a further embodiment of the present disclosure there is included, a method of predicting hydrophobicity of a peptide:

(a) measuring retention time for each peptide of a standard peptide mixture at three or more different concentrations of acetonitrile under isocratic conditions;

(b) calculating a retention coefficient k for each peptide in the mixture and at each concentration of acetonitrile using equation (2)

$$k=(t_R-t_O)/T_{Oc} \qquad (2)$$

wherein
$t_R$ is the retention time,
$t_O$ is system dead time, and
$T_{Oc}$ is column dead time;

(c) for each peptide in the mixture, plotting log k vs φ, wherein φ is the acetonitrile volume fraction;

(d) for each peptide in the mixture, determining the value of φ when log k=1 and converting this to acetonitrile concentration to provide a universal hydrophobicity index (UHI);

(e) plotting retention times of each peptide vs its UHI;

(f) determining the retention time of an unknown peptide under the isocratic liquid chromatographic conditions; and (g) determining from the plot in (e) the value of UHI that corresponds to the retention time of the unknown peptide, wherein the UHI correlates to the hydrophobicity of the unknown peptide.

Table 2 shows UHI values for P1-P6 standard peptides in four various sorbent/eluent combinations. These combinations correspond to four popular sets of RP HPLC conditions applied in proteomics and their corresponding SSRCalc models.

In an embodiment of the disclosure the retention time is measured at five or more different acetonitrile concentrations.

The unknown peptide is any peptide, including mixtures of peptides, that one wishes to study. The unknown peptide may be synthetic or from natural sources.

In embodiments of the disclosure the selected liquid chromatographic conditions are varied by changing the type of sorbent, the nature and concentration of the ion-pairing modifier and the temperature. In a further embodiment the liquid chromatographic conditions are standard RP HPLC conditions selected from 100 Å-TFA, 300 Å-TFA, 100 Å-FA and 100 Å-pH 10.

Application of the UHI in Proteomics

The universal hydrophobicity index (UHI) may be applied in proteomics and for peptide RP HPLC method development. For example the UHI may be used for "chromatographic" calibration of LC-MS data when retention prediction procedures are used for enhancement of proteomics analysis, the alignment of LC-MS data collected using different instrumental set ups and facilitating the transfer of retention data obtained in proteomics experiments or hydrophobicity calculations into analytical/preparative scale HPLC.

Chromatographic Calibration of LC-MS Runs

In an embodiment of the disclosure the method of predicting hydrophobicity of a peptide described above is used in an LC-MS workflow. As a first step, a sample is spiked with the appropriate amount of peptide retention standard. Analysis of the spiked sample is run and the peaks of the standard peptides are identified, then a linear plot of RT vs. ideal hydrophobicity or UHI is generated. The linear plot is used directly to assign retention time prediction errors for the detected sample species. In a particular embodiment of the specification this procedure is used in conjunction with LC-MALDI MS fingerprinting protocols. In another embodiment the procedure is used in conjunction with searching using MAss and Retention Time (SMART).[33] This search engine can process mixtures of up to 100 proteins in 1 D LC-MALDI format at 10 ppm mass accuracy. In a further embodiment, in HPLC-ESI format, the calculated retention prediction errors can be used to filter false positive MS/MS identifications. In still a further embodiment it can be used in conjunction with the Accurate Mass retention Time (AMT) approach.

Alignment of LC-MS Data

In a further embodiment of the disclosure the universal hydrophobicity index can be used to align peptide retention data sets on both intra- and inter-laboratory levels. These data sets can be used for the optimization of prediction models and as a source of measured retention values ("ideal" or measured hydrophobicities"), which can be used directly in identification protocols instead of the calculated values (call "lookup mode"). Since most of proteomics experiments are performed using nano- and micro-flow LC setups, it is difficult to provide the required accuracy of gradient delivery even within the same LC system, never mind using different ones. In a particular embodiment, the sample to be analyzed is spiked with a set of calibrating peptides. The LC-MS analysis of the sample is run on the first LC-MS system and a linear plot of RT vs. UHI of (ideal hydrophobicity) is generated. From this plot it is possible to determine the conversion factor from the first system to a second LC-MS system where the same calibrating peptides have also been analyzed. Using the conversion factor and the retention time of the sample constituents in the first system the retention time of the sample constituents can be predicted for the second system. In a further embodiment the calibration sample is the peptide composition of the present disclosure. In another embodiment a collection of massive data sets could be prepared for a general consensus of chromatographic conditions. In a particular embodiment the fixed condition would be the types of sorbent and ion-pairing modifier, while the column size, flow-rate and slope of the gradient could vary.

Preparative LC Method Development—Transfer of Proteomics Data to Shallow Gradient Conditions.

In another embodiment of the disclosure the universal hydrophobicity index is used to predict preparative scale LC conditions based on proteomics data or to predict conditions for LC in shallow gradient conditions. In a particular embodiment, a sample is spiked with a peptide retention standard. Analysis of the sample allows direct assignment of UHI values for all identified separated species. The UHI hydrophobicity can be compared to known UHI hydrophobicities. In a particular embodiment the measured UHI value can be compared to a set of ~300 tryptic peptides generated from human/ bovine transferrin/albumin and horse myoglobin mixture separated using the four sets of chromatographic conditions described above. These data were obtained using micro-flow off-line LC-MALDI MS. When purification of particular component from this mixture is required, the UHI value for this peptide can be used to choose a-priori starting acetonitrile concentration to minimize time for the method development. In another embodiment, purification methods for newly synthesized peptides can be determined by calculating SSRCalc in the retention prediction model and converting this value to the corresponding UHI value and following the procedure described above. In a particular embodiment the peptide retention standard is the peptide composition described herein.

The following non-limiting examples are illustrative of the present disclosure:

EXAMPLES

Materials and Methods

Reagents.

Deionized (18 MΩ) water and HPLC-grade acetonitrile were used for the preparation of eluents. All chemicals (including the purified proteins) were sourced from Sigma Chemicals (St-Louis, Mo.) unless otherwise noted. Sequencing-grade modified trypsin (Promega, Madison, Wis.) was used for digestion. The six peptides (referred to hence as P1-P6)—LGGGGGGDGSR, LGGGGGGDFR, LLGGGGDFR, LLLGGDFR, LLLLDFR, LLLLLDFR— were custom synthesized by BioSynthesis Inc. (Lewisville, Tex.); ALILTLVS was purchased from Bachem. The peptide retention standard S1-S5 described in the introduction was purchased from Pierce (Rockford, Ill.).

Protein Digestion.

A tryptic digest of a 5 protein mixture [(human/bovine) transferrin and albumin, plus horse myoglobin] was used for microLC-MALDI MS experiments. Proteins were reduced (10 mM dithiothreitol, 30 min, 57° C.), alkylated (50 mM iodoacetamide, 30 min in the dark at room temperature), dialysed (100 mM $NH_4HCO_3$, 6 hours, 7 kDa MWCO, Pierce) and digested with trypsin (1/50 enzyme/substrate weight ratio, 12 hours, 37° C.). This protein digest was diluted prior the injection and spiked with mixture of the 6 peptides to provide ~1-2 pmol per injection for all components.

Chromatography.

Two chromatographic setups: micro-flow 3 μl/min and "semi-micro" at 150 μl/min were employed utilizing a micro-Agilent 1100 Series system (Agilent Technologies, Wilmington, Del.) with two column sizes: 300 μm×150 mm (micro) and 1 mm×100 mm (semi-micro). The three stationary phases studied included: Vydac 218 TP C18, 300 Å pore size, 5 μm (Grace Vydac, Hesperia, Calif.); Luna C18(2) 100 Å, 5 μm (Phenomenex, Torrance, Calif.) and XTerra C18, 120 Å, 5 μm (Waters, Milford, Mass.). Three different ion-pairing systems with linear water-acetonitrile gradients were employed: 0.1% trifluoroacetic acid (TFA) in both eluents A and B (Vydac and Luna), 0.1% formic acid (FA, Luna) and 20 mM ammonium formate pH 10 (XTerra). This provided us with four different mobile/stationary phase combinations corresponding to four versions of SSRCalc model: 100 and 300 Å for TFA, 100 Å with FA and 100 Å at pH 10. Gradient separations of the 6-peptide mixture in "semi-micro" flow mode were performed in all four systems using 0.5, 1, 2 and 4% acetonitrile per minute gradient slopes.

Stock solutions of the 6 custom peptides (~1 mg/ml) were prepared by dissolving in 1 ml of 0.1% TFA in water (20% acetonitrile for peptides #5 and 6). Ten microliters sample injection was applied for "semi-micro" conditions in both isocratic and gradient modes. Individual peptides, their mixture and the S1-S5 retention standard were diluted to provide ~0.5-1 µg injection of each component. 214 nm UV detection was used. All chromatographic experiments were conducted at room temperature, ~25° C. Dead volume of the column and connecting tubings was measured using injection of non-retained compound (water) and measuring elution time of negative peak. Retention coefficients for isocratic elution were calculated using the formula: $k=(t_R-t_0)/t_{0c}$; where $t_R$ is retention time, $t_0$ and $t_{0c}$—system (column and tubings) and column dead time.

In micro-flow LC-MALDI MS experiments, the samples (5 µL, ~2 pmole each of protein digest and 6 calibrating peptides per injection) were injected directly onto a 300 µm×150 mm RP columns and eluted with a linear 0-50% acetonitrile gradient over 50 min. The column effluent (3 µL/min) was mixed on-line with 2,5-dihydroxybenzoic acid MALDI matrix solution and deposited by a computer-controlled robot onto a movable MALDI target at 0.5-min intervals. One hundred fractions were collected, air-dried and subjected to MALDI-MS analysis.

TOF Mass Spectrometry.

The Manitoba/Sciex prototype MALDI quadrupole/TOF (QqTOF) mass spectrometer was used to confirm peak identity in "semi-micro" mode and for micro-LC MS fingerprint of 5-protein digest mixture. Orthogonal injection of ions from the quadrupole into the TOF section normally produces a mass resolving power of ~10,000 FWHM, and accuracy within a few mDa in the TOF spectra in both MS and MS/MS modes.

Example 1

Figure 2:
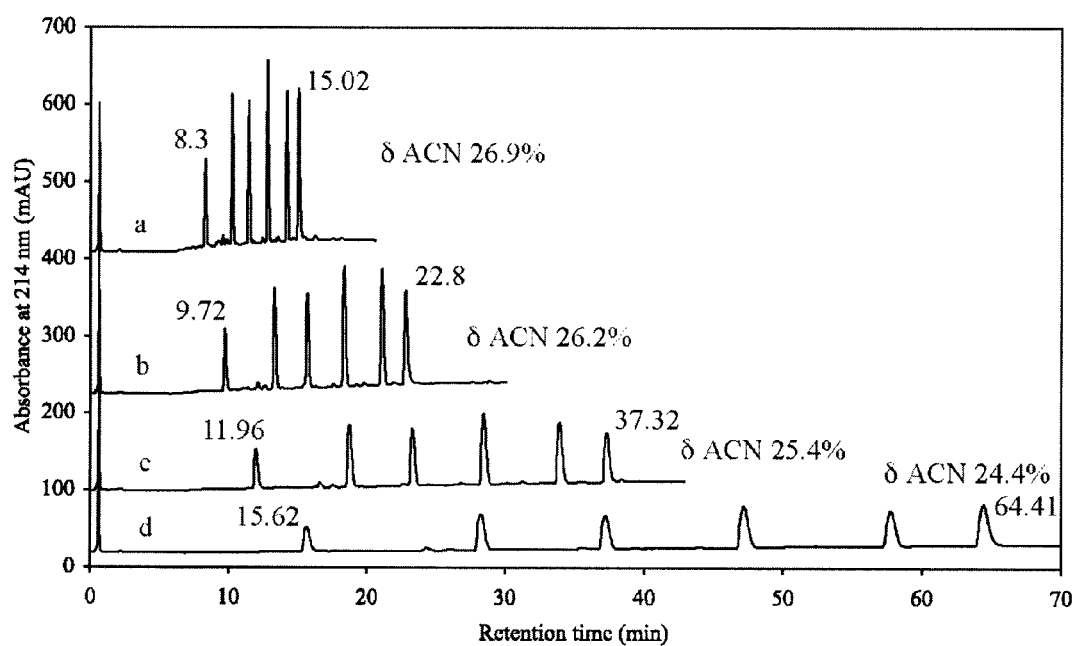
FIG. 2 is a graph showing chromatographic separation of a 6-peptide mixture according to one embodiment of the present disclosure using different gradient slopes a-b—4%, 2%, 1% and 0.5% acetonitrile per minute. Luna C18(2), 1×100 mm, 150 µl/min flow-rate, 0.1% TFA in both eluents A and B. Retention times of first and 6$^{th}$ peptides are shown.

Measuring Peptide Hydrophobicity Under Gradient Conditions: The Influence of Gradient Slope The six-peptide mixture was separated using 4, 2, 1 and 0.5% acetonitrile per minute gradients in all 4 chromatographic systems. FIG. 2 shows UV traces for Luna C18(2) and 0.1% TFA. The time difference between first and last peaks multiplied by the slope of the gradient gives ACN % range (δ ACN) covered by the standard. Discounting the possible variations in S slopes in the LSS equation for different peptides, one would expect these to be constant. The actual values were found to decrease systematically: 26.9, 26.2, 25.4 and 24.4 ACN %. The same trend of narrowing the ACN % scale for shallower gradients was observed for all four LC systems used (results not shown here). This shift could result in a significant error during determination of acetonitrile concentration at which a particular component elutes from the column. Because peptides elute from RP columns in a very narrow range of organic solvent concentration, this in-turn will complicate the method transfer between gradient and isocratic (or shallow gradient) conditions. For example, taking into account gradient delay time of the system (4.3 min) and the retention time of peptide P5 (FIG. 2c), we calculated concentration of acetonitrile required for elution of P5 is 29.6%. The measurement of retention under isocratic conditions (see FIG. 3), shows that the elution starts much earlier: k=10 at 26.1%.

Interestingly, Guo et al. performed similar experiments for S1-S5 peptides and even though some non-linearity was found, deviations were considered negligible. Most likely it was a consequence of having almost identical peptide sizes and hydrophobicities in the S1-S5 mixture. Extending hydrophobicity range and performing isocratic measurements to generate log k vs. φ dependences for P1-P6 peptides should help to clarify this effect.

Example 2

Measuring Peptide Hydrophobicity in RP HPLC Using Isocratic Conditions

Figure 3:
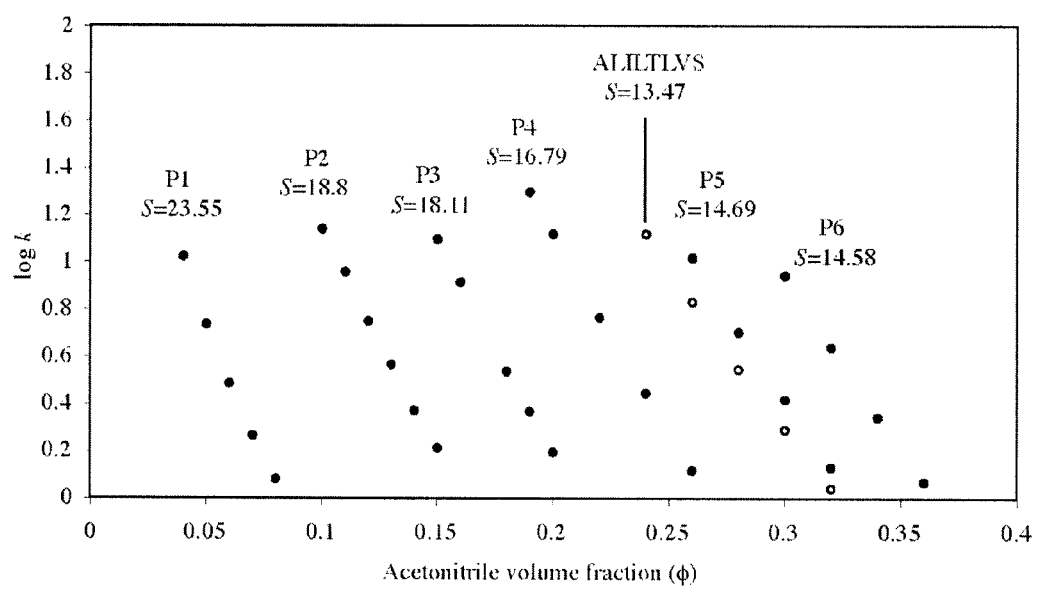
FIG. 3 is a graph of log k vs. φ plots for studied peptides using Luna C18(2) column and TFA as modifier. ●—P1-P6 peptides; ○—ALILTLVS [SEQ ID NO:8].

Since accurate measurement of ACN % hydrophobicity using gradient elution is problematic it is proposed to use isocratic conditions for this purpose. FIG. 3 shows log k vs. φ plots for 6 studied peptides separated on Luna C18(2) column with TFA as ion-pairing modifier measured under isocratic conditions. This confirms once again that peptides elute from reversed-phase sorbents within a very narrow range of acetonitrile concentration. It is clear as well that the slope of these dependencies decrease systematically as peptide hydrophobicity increase. This is the reason for narrowing ACN percentage scale for shallow gradients in FIG. 2.

It is proposed to use acetonitrile concentration at which the capacity factor of any given peptide is equal to 10 (at room temperature ~25° C.) as a measure of peptide hydrophobicity. This value is referred to herein as peptide Universal Hydrophobicity Index (UHI), since it depends only on type of the sorbent and ion-pairing modifier. UHI values can be measured by extrapolating of log k=1 on φ axis in FIG. 3. Table 2 shows UHI values for P1-P6 standard peptides in four various sorbent/eluent combinations. These combinations correspond to four popular sets of RP HPLC conditions applied in proteomics and their corresponding SSRCalc models.

Example 3

Linear-Solvent-Strength Theory for the Peptide Separation

The general theory of gradient separation of biopolymers matured in the 1980's and 1990's. Peptides and proteins seem to behave similarly to small organic molecules under RP conditions and follow the basic LSS equation (1). The only differences were found at extremely high S values.[4] In other words, a dramatic change in peptide retention is observed with small changes in acetonitrile concentration. Originally it was proposed that the S value for peptide/protein depends on its molecular weight: $S \sim 0.44M^2$.[29] Later measurements on tryptic digests of recombinant human growth hormone (rhGH) showed this was an incorrect generalization;[30-32] the S values for 21 major products in this digest ranged from 14.2 to 32.7 and exhibited no correlation with the size of the species. For example T14 QTYSK [SEQ ID NO:9] and T9 ISLLLIQSWLEPVQFLR [SEQ ID NO:10] products have S-values of 24.3 and 18.5. To date this behavior is still not understood.

The six peptides used in the present study have nearly identical molecular weights but show almost 2-fold variations in S values of P1 and P6, suggesting that the slopes in the basic LSS equation for peptide separation are strongly affected by peptide hydrophobicity. In addition to the described peptides, the isocratic retention of singly charged at pH 2 ALILTLVS [SEQ ID NO:8] (FIG. 3) was measured. It has comparable molecular weight and hydrophobicity to peptide #5, with only one significant difference—absence of a positive charge on C-terminal side. This could be the reason why it showed lower S value: 13.47 vs. 14.69 for P5. Additional proof of this hypothesis is provided by the analysis of the previously mentioned rhGH data.[32] Thus, T14 QTYSK

[SEQ ID NO:9] peptide exhibited 24.3 S-value, while it's product of N-terminal cyclization T14c exhibits an S-value of only 15.7. The difference between these two molecules is the absence of a positively charged N-terminus due to Gln conversion into pyroglutamic acid. The highest S-values (above 30) were measured for two disulfide-linked fragments T6-16SS and T6-16cSS—these species carry a larger number of positively charged groups at acidic pH.

Collectively these observations indicate that S values in peptide/protein RP HPLC likely depend on various factors: molecular weight, charge and hydrophobicity. It is believed that LSS for peptide/protein separation require some adjustments in the light of these findings. It is interesting to note how the effect of peptide charge highlights the importance of taking into account ion-pairing processes for correct understanding of the separation mechanism. This effect was a key component in developing our SSRCalc algorithm[11]—one of the first models that deal effectively with sequence variations for peptide retention prediction.

Example 4

Application of Standard Peptide Mixtures in Proteomics and for Peptide RP HPLC Method Development At the moment there are major areas of application for peptide mixture described here (or similar ones) in association with UHI concept: "chromatographic" calibration of LC-MS data when retention prediction procedures are used for enhancement of proteomics analysis; the alignment of LC-MS data collected using different instrumental set ups; and facilitating the transfer of retention data obtained in proteomics experiments or hydrophobicity calculations into analytical/preparative scale HPLC. The first two applications will be effective independently from the form of hydrophobicity expression: SSRCalc hydrophobicity units or UHI. The third application requires expression in UHI, as knowing the exact ACN % elution window of particular a peptide is a factor in preparative LC method development.

Figure 4:
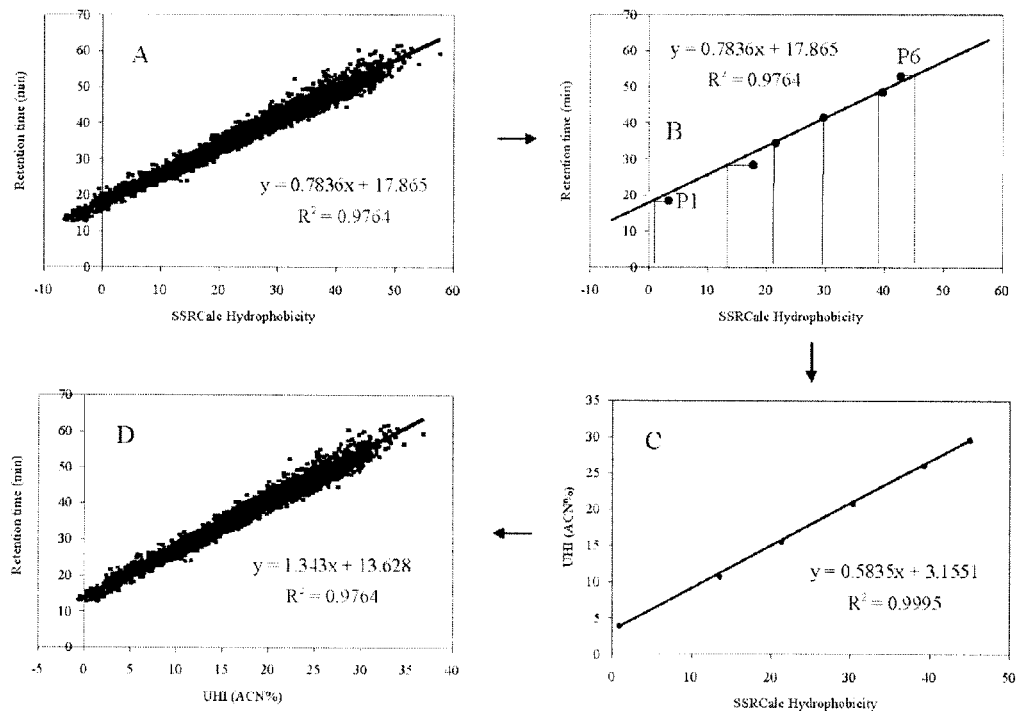
FIG. 4 is a series of graphs showing the conversion of SSRCalc hydrophobicity values into UHI scale. a) current accuracy of 100 Å TFA model for optimization data set; b) determination of "ideal" hydrophobicity values for P1-P6 standard; c) conversion of unitless SSRCalc hydrophobicity into UHI ACN % scale; d) RT vs. UHI plot for 100 Å TFA model.

The procedure of transfer of calculated hydrophobicity into UHI scale is depicted in FIG. 4, using 100 Å SSRCalc model as an example. Current optimization data set for 100 Å SSRCalc contains ~5000 peptides and exhibit ~0.975 $R^2$-value correlation retention time vs. hydrophobicity (FIG. 4a). Peptides P1-P6 are a part of this set and their "ideal" or measured hydrophobicities can be obtained by extrapolation of their experimental retention times onto the x axis of this plot (FIG. 4b). Not surprisingly, there is a near perfect linear correlation between P1-P6 measured SSRCalc hydrophobicities and their UHI values (FIG. 4c; UHI=H*0.5835+3.1551), which can be used for the conversion. RT vs. UHI dependence for the 100 Å SSRCalc optimization data set is shown in FIG. 4d. Resulting dependence represents much more clearly entire RP HPLC separation procedure. Thus, vast majority of peptides comprising the present data set have UHI values (elute from C18 100 Å column) between 0 and 35% acetonitrile when 0.1% TFA used as ion pairing modifier.

(a) Chromatographic Calibration of LC-MS Runs

When peptide retention prediction procedures are used in an LC-MS workflow, the sample should be spiked with the appropriate amount of peptide retention standard. Following peak assignment of the standard peptides, the linear plot RT vs. ideal hydrophobicity or UHI is generated. It can then be used directly to assign retention time prediction errors for the detected species. This procedure was used in conjunction with LC-MALDI MS fingerprinting protocol. In 2006, Search using MAss and Retention Time (SMART) was introduced.[33] This search engine can process mixtures of up to 100 proteins in 1 D LC-MALDI format at 10 ppm mass accuracy. In HPLC-ESI format, the calculated retention prediction errors can be used to filter false positive MS/MS identifications or in conjunction with the Accurate Mass retention Time (AMT) approach.

(b) Alignment of LC-MS Data

These procedures are very important for collection of peptide retention data sets on both intra- and inter-laboratory levels. These data sets can be used for the optimization of prediction models and as a source of measured retention values ("ideal" or measured hydrophobicities"), which can be used directly in identification protocols instead of the calculated values (this is called "lookup mode"). Since most of proteomics experiments are performed using nano- and micro-flow LC setups, it is difficult to provide the required accuracy of gradient delivery even within the same LC system, never mind using different ones. Spiking the samples with the set of calibrating peptides and plotting RT vs. UHI linear plots for each chromatogram makes this conversion easy. It is conceivable that the collection of massive data sets should be done for a general consensus of chromatographic conditions: fixed types of the sorbent and ion-pairing modifier, while the column size, flow-rate and slope of the gradient could vary.

TABLE 1

Amino acid sequences, m/z values and calculated hydrophobicities for 6-peptide standard mixture.

| Peptide sequence | M/z (1+) | M/z (2+) | H 100 Å TFA | H 300 Å TFA |
|---|---|---|---|---|
| LGGGGGGDGSR [SEQ ID NO: 2] | 889.413 | 445.2105 | 3.25 | 4.44 |
| LGGGGGGDFR [SEQ ID NO: 3] | 892.428 | 446.718 | 17.68 | 16.28 |
| LLGGGGDFR [SEQ ID NO: 4] | 891.469 | 446.2385 | 21.5 | 21.57 |
| LLLGGDFR [SEQ ID NO: 5] | 890.51 | 445.759 | 29.7 | 29.07 |
| LLLLDFR [SEQ ID NO: 6] | 889.551 | 445.2795 | 39.66 | 37.44 |
| LLLLLDFR [SEQ ID NO: 7] | 1002.635 | 501.8215 | 42.73 | 42.49 |

TABLE 2

UHI values of 6-peptide standard mixture in four different chromatographic systems.

| Peptide sequence | 100 Å C18 - TFA | 300 Å C18 - TFA | 100 Å C18 - FA | 100 Å C18 - pH 10 |
|---|---|---|---|---|
| LGGGGGGDGSR [SEQ ID NO: 2] | 3.97 | 1.89 | <0 | 1.14 |
| LGGGGGGDFR [SEQ ID NO: 3] | 10.74 | 8.40 | 4.58 | 6.80 |
| LLGGGGDFR [SEQ ID NO: 4] | 15.53 | 13.35 | 8.55 | 13.65 |

TABLE 2-continued

UHI values of 6-peptide standard mixture in four different chromatographic systems.

| Peptide sequence | 100 Å C18 – TFA | 300 Å C18 – TFA | 100 Å C18 – FA | 100 Å C18 – pH 10 |
|---|---|---|---|---|
| LLLGGDFR [SEQ ID NO: 5] | 20.72 | 18.90 | 13.08 | 18.29 |
| LLLLDFR [SEQ ID NO: 6] | 26.07 | 24.78 | 18.26 | 24.18 |
| LLLLLDFR [SEQ ID NO: 7] | 29.58 | 28.60 | 21.59 | 28.94 |

FULL CITATIONS FOR DOCUMENTS REFERRED TO IN THE SPECIFICATION

1. Hearn, M. T. W.; Ed., *HPLC of Proteins and Polynucleotides. Contemporary Topics and Applications*. Wiley; New York: 1991.
2. Snyder, L. R.; Glajch, J. L.; Kirkland, J. J. *Practical HPLC Method Development*. Wiley; New York: 1997.
3. Mant, C. T.; Hodges, R. S. *In HPLC of Biological Macromolecules*; Marcel Dekker: New York, 2002; pp 433-511.
4. Snyder, L. R.; Dolan J. W. *High-Performance Gradient Elution: The Practical Application of the Linear-Solvent-Strength Model*. Wiley; New York: 2006.
5. Palmblad, M.; Ramström, M.; Markides, K. E.; Håkansson, P.; Bergquist, J. *Anal. Chem.* 2002, 74, 5826-5830.
6. Strittmatter, E. F.; Kangas, L. J.; Petritis, K.; Mottaz, H. M.; Anderson, G. A.; Shen, Y.; Jacobs, J. M.; Camp, D. G. $2^{nd}$; Smith, R. D. *J Proteome Res.* 2004, 3, 760-769.
7. Strittmatter, E. F.; Ferguson, P. L.; Tang, K.; Smith, R. D. *J Am Soc Mass Spectrom.* 2003, 14, 980-991.
8. Krokhin, O. V.; Ying, S.; Cortens, J. P.; Ghosh, D.; Spicer, V.; Ens, W.; Standing, K. G.; Beavis, R. C.; Wilkins J. A. *Anal. Chem.* 2006, 78, 6265-6269.
9. Dwivedi, R. C.; Spicer, V.; Harder, M.; Antonovici, M.; Ens, W.; Standing, K. G.; Wilkins, J. A., Krokhin, O. V. *Anal. Chem.* 2008, in press.
10. Krokhin, O. V.; Craig, R.; Spicer, V.; Ens, W.; Standing, K. G.; Beavis, R. C.; Wilkins, J. A. *Mol Cell Proteomics.* 2004, 3, 908-919.
11. Krokhin, O. V. *Anal. Chem.* 2006, 78, 7785-7795.
12. Shinoda, K.; Sugimoto, M.; Yachie, N.; Sugiyama, N.; Masuda, T.; Robert, M.; Soga, T.; Tomita, M. *J Proteome Res.* 2006, 5, 3312-3317.
13. Petritis, K.; Kangas, L. J.; Yan, B.; Monroe, M. E.; Strittmatter, E. F.; Qian, W. J.; Adkins, J. N.; Moore, R. J.; Xu. Y.; Lipton, M. S.; Camp, D. G. $2^{nd}$; Smith, R. D.; *Anal Chem.* 2006, 78, 5026-5039.
14. Gorshkov, A. V.; Tarasova, I. A.; Evreinov, V. V.; Savitski, M. M.; Nielsen, M. L.; Zubarev, R. A.; Gorshkov, M. V. *Anal Chem.* 2006, 78, 7770-7777.
15. Klammer, A. A.; Yi, X.; Maccoss, M. J.; Noble, W. S. *Anal Chem.* 2007, 79, 6111-6118.
16. Meek, J. L. *Proc. Natl. Acad. Sci. U.S.A.* 1980, 77, 1632-1636.
17. Browne, C. A.; Bennett, H. P. J.; Solomon, S. *Anal. Biochem.* 1982, 124, 201-208.
18. Guo, D.; Mant, C. T.; Taneja, A. K.; Parker, J. M. R.; Hodges, R. S. *J. Chromatogr.* 1986, 359, 499-517.
19. Su, S. J.; Grego, B.; Niven, B.; Hearn, M. T. W. *J. Liq. Chromatogr.* 1981, 4, 1745-1753.
20. Tripet, B.; Cepeniene, D.; Kovacs, J. M.; Mant, C. T.; Krokhin, O. V.; Hodges, R. S. *J Chromatoger A.* 2007, 1141(2), 212-225.
21. Glaich, J. L., Quarry, M. A., Vasta, J. F., Snyder, L. R. *Anal Chem.* 1986, 58, 280-285.
22. Spicer, V.; Yamchuk, A.; Cortens, J.; Sousa, S.; Ens, W.; Standing, K. G.; Wilkins, J. A.; Krokhin, O. V. *Anal. Chem.* 2007, 79, 8762-8768.
23. Petritis, K.; Kangas, L. J.; Ferguson, P. L.; Anderson, G. A.; Pasa-Tolic, L.; Lipton, M. S.; Auberry, K. J.; Strittmatter, E. F.; Shen, Y.; Zhao, R.; smith, R. D. *Anal. Chem.* 2003, 75, 1039-1048.
24. May, D.; Fitzgibbon, M.; Liu, Y.; Holzman, T.; Eng, J.; Kemp, C. J.; Whiteaker, J.; Paulovich, A.; McIntosh, M. *J Proteome Res.* 2007, 6, 2685-2694.
25. Guo, D.; Mant, C. T.; Taneja, A. K.; Hodges, R. S. *J Chromatogr.* 1986, 359, 519-532.
26. Eyers, C. E.; Simpson, D. E.; Wong, S. C. C.; Beynon, R. J.; Gaskell, S. J. *J. Am Soc Mass Spectrom.* 2008, in press.
27. J. Janin, Surface and Inside Volumes in Globular Proteins, *Nature,* 277(1979)491-492.
28. J. Kyte and R. F. Doolittle, A Simple Method for Displaying the Hydropathic Character of a Protein, *J. Mol Biol.* 157(1982)105-132.
29. Cornette, J.; Cease, K. B.; Margalit, H.; Spouge, J. L.; Berzofsky J. A. and C. DeLisi, Hydrophobicity Scales and Computational Techniques for Detecting Amphipathic Structures in Proteins, *J. Mol. Biol.* 195(1987)659-685.
29. Stadalius, M. A.; Gold, H. S.; Snyder, L. R. *J. Chromatogr.* 1984, 296, 31-59.
30. Grego, B.; Lambrou, F.; Hearn, M. T. W. *J. Chromatogr.* 1983, 266, 89-103.
31. Chloupek, R. C., Hancock, W. S., Snyder, L. R. *J. Chromatogr.* 1992, 594, 65-73.
32. Hancock, W. S.; Chloupek, R. C.; Kirkland, J. J.; Snyder, L. R. *J. Chromatogr. A* 1994, 686, 31-43.
33. Krokhin, O. V.; Spicer, V.; Standing, K. G.; Wilkins J. A.; Ens, W. $54^{th}$ ASMS Conference on Mass Spectrometry and Allied topics, Seattle, USA, poster 2006.

What is claimed is:

1. A composition comprising one or more of the following peptides:

| | |
|---|---|
| LGGGGGGDGSR; | [SEQ ID NO: 2] |
| LGGGGGGDFR; | [SEQ ID NO: 3] |
| LLGGGGDFR; | [SEQ ID NO: 4] |
| LLLGGDFR; | [SEQ ID NO: 5] |
| LLLLDFR; or | [SEQ ID NO: 6] |
| LLLLLDFR | [SEQ ID NO: 7]. |

2. The composition of claim 1 comprising two, three, four, five or six of the following peptides:

```
LGGGGGGDGSR;        [SEQ ID NO: 2]
LGGGGGGDFR;         [SEQ ID NO: 3]
LLGGGGDFR;          [SEQ ID NO: 4]
LLLGGDFR;           [SEQ ID NO: 5]
LLLLDFR;            [SEQ ID NO: 6]
or
LLLLLDFR            [SEQ ID NO: 7].
```

3. The composition of claim 1 comprising:

```
LGGGGGGDGSR;        [SEQ ID NO: 2]
LGGGGGGDFR;         [SEQ ID NO: 3]
LLGGGGDFR;          [SEQ ID NO: 4]
LLLGGDFR;           [SEQ ID NO: 5]
LLLLDFR;            [SEQ ID NO: 6]
and
LLLLLDFR            [SEQ ID NO: 7].
```

4. The composition of claim 1 consisting of:

```
LGGGGGGDGSR;        [SEQ ID NO: 2]
LGGGGGGDFR;         [SEQ ID NO: 3]
LLGGGGDFR;          [SEQ ID NO: 4]
LLLGGDFR;           [SEQ ID NO: 5]
LLLLDFR;            [SEQ ID NO: 6]
and
LLLLLDFR            [SEQ ID NO: 7].
```

5. A kit for use as a standard for peptide chromatography comprising a composition of claim 1 and instructions for use.

6. A method of predicting hydrophobicity of a peptide under selected liquid chromatography conditions comprising:
   (a) measuring retention time for each peptide of a standard peptide mixture at three or more different concentrations of acetonitrile under isocratic conditions;
   (b) calculating a retention coefficient k for each peptide in the mixture and at each concentration of acetonitrile using equation (2)
   $$k=(t_R-t_O)/T_{Oc} \qquad (2)$$
   wherein
   $t_R$ is the retention time,
   $t_O$ is system dead time, and
   $T_{Oc}$ is column dead time;
   (c) for each peptide in the mixture, plotting log k vs $\phi$, wherein $\phi$ is the acetonitrile volume fraction;
   (d) for each peptide in the mixture, determining the value of $\phi$ when log k=1 and converting this to acetonitrile concentration to provide a universal hydrophobicity index (UHI);
   (e) plotting retention times of each peptide vs its UHI;
   (f) determining the retention time of an unknown peptide under the isocratic liquid chromatographic conditions; and
   (g) determining from the plot in (e) the value of UHI that corresponds to the retention time of the unknown peptide,
   wherein the UHI correlates to the hydrophobicity of the unknown peptide.

7. The method according to claim 6, wherein the standard peptide mixture is a composition comprising;

```
LGGGGGGDGSR;        [SEQ ID NO: 2]
LGGGGGGDFR;         [SEQ ID NO: 3]
LLGGGGDFR;          [SEQ ID NO: 4]
LLLGGDFR;           [SEQ ID NO: 5]
LLLLDFR;            [SEQ ID NO: 6]
and
LLLLLDFR            [SEQ ID NO: 7].
```

* * * * *

SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Synthetic construct
<220> FEATURE:

```
<221> NAME/KEY: MISC_FEATURE
<222> LOCATION: (3)..(4)
<223> OTHER INFORMATION: X-X = [Gly-Gly], [Ala-Gly], [Val-Gly] and
      [Val-Val]
<220> FEATURE:
<221> NAME/KEY: MISC_FEATURE
<222> LOCATION: (3)..(4)
<223> OTHER INFORMATION: When X-X is [Ala-Gly] peptide has additional
      N-Terminal amino group

<400> SEQUENCE: 1

Arg Gly Xaa Xaa Gly Leu Gly Leu Gly Lys
1               5                   10

<210> SEQ ID NO 2
<211> LENGTH: 11
<212> TYPE: PRT
<213> ORGANISM: Artificial sequence
<220> FEATURE:
<223> OTHER INFORMATION: Synthetic construct

<400> SEQUENCE: 2

Leu Gly Gly Gly Gly Gly Gly Asp Gly Ser Arg
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthetic construct

<400> SEQUENCE: 3

Leu Gly Gly Gly Gly Gly Gly Asp Phe Arg
1               5                   10

<210> SEQ ID NO 4
<211> LENGTH: 9
<212> TYPE: PRT
<213> ORGANISM: Artificial sequence
<220> FEATURE:
<223> OTHER INFORMATION: Synthetic construct

<400> SEQUENCE: 4

Leu Leu Gly Gly Gly Gly Asp Phe Arg
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic construct

<400> SEQUENCE: 5

Leu Leu Leu Gly Gly Asp Phe Arg
1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Synthetic construct

<400> SEQUENCE: 6

Leu Leu Leu Leu Asp Phe Arg
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic construct

<400> SEQUENCE: 7

Leu Leu Leu Leu Leu Asp Phe Arg
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic construct

<400> SEQUENCE: 8

Ala Leu Ile Leu Thr Leu Val Ser
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic construct

<400> SEQUENCE: 9

Gln Thr Tyr Ser Lys
1               5

<210> SEQ ID NO 10
<211> LENGTH: 17
<212> TYPE: PRT
<213> ORGANISM: Artificial sequence
<220> FEATURE:
<223> OTHER INFORMATION: Synthetic construct

<400> SEQUENCE: 10

Ile Ser Leu Leu Leu Ile Gln Ser Trp Leu Glu Pro Val Gln Phe Leu
1               5                   10                  15

Arg
```